United States Patent [19]

Patterson et al.

[11] Patent Number: 5,248,495
[45] Date of Patent: Sep. 28, 1993

[54] POST FOAMING SHAVING GEL COMPOSITION

[75] Inventors: Thomas S. Patterson; Alejandro Cedeno, both of Cincinnati; John G. DuVall, Hamilton, all of Ohio

[73] Assignee: The Procter & Gamble Company, Cincinnati, Ohio

[21] Appl. No.: 869,994

[22] Filed: Apr. 16, 1992

[51] Int. Cl.$^5$ ............................................. A61K 7/15
[52] U.S. Cl. ........................................ 424/73; 424/47
[58] Field of Search ..................................... 424/47, 73

[56] References Cited

U.S. PATENT DOCUMENTS

| | | | |
|---|---|---|---|
| 3,228,842 | 1/1966 | Markland et al. | 167/87 |
| 3,330,730 | 7/1967 | Hernandez | 167/85 |
| 3,655,865 | 4/1972 | Murphy | 424/45 |
| 3,923,970 | 12/1975 | Breuer | 424/47 |
| 4,078,105 | 3/1978 | Shapiro et al. | 427/417 |
| 4,528,111 | 7/1985 | Su | 252/107 |
| 4,957,732 | 9/1990 | Grollier et al. | 424/73 |
| 5,034,220 | 7/1991 | Helioff et al. | 424/73 |

FOREIGN PATENT DOCUMENTS

| | | |
|---|---|---|
| 91/07943 | 6/1991 | PCT Int'l Appl. . |
| 1279145 | 6/1972 | United Kingdom . |
| 1444334 | 7/1976 | United Kingdom . |

OTHER PUBLICATIONS

Dow Corning, Form No. 24-414B-87.

Primary Examiner—Thurman K. Page
Assistant Examiner—Neil Levy
Attorney, Agent, or Firm—Michael E. Hilton; John M. Howell; Steven J. Goldstein

[57] ABSTRACT

Shaving gel compositions having excellent shaving properties and skin conditioning benefits. These compositions are found to be stable, despite the removal of the secondary surfactant.

19 Claims, No Drawings

ID COMPOSITION

TECHNICAL FIELD

The present invention relates to post-foaming shaving gel compositions absent a secondary non-ionic surfactant having excellent skin conditioning properties.

BACKGROUND OF THE INVENTION

The practice of removing hair from the body extends back through recorded history. A number of different methods to remove hair have been used. Shaving hairs or whiskers off at skin level using a sharpened blade, or razor, is probably the best known of such methods.

Topical compositions, or shaving aids are continually being developed not only to make shaving easier, but, to achieve a closer, less skin irritating shave. One such composition is a shaving cream. Shaving creams are used particularly by men for removing beard growth from their faces; aerosol shaving creams being the best known. Aerosol shaving creams, usually packaged in pressurized metal cans, are white, voluminous, creamy foams, are disclosed in U.S. Pat. Nos. 3,330,730, Hernandez, issued Jul. 11, 1967; 3,655,865, Murphy, issued Apr. 11, 1972 and 3,923,970, Breuer, issued Dec. 2, 1975.

A relatively recent shaving composition is the post-foaming shaving gel. These compositions are designed to be dispensed from the can as a clear, translucent gel, which is converted to a foam when rubbed into the palm or against the face. Such compositions are described in U.S. Pat. Nos. 3,541,581, Monson, issued Nov. 17, 1970; 4,528,111, Su, issued Jul. 9, 1985; U.S. 4,957,732, Grollier et al., issued Sep. 18, 1990; 5,034,220, Helioff et al, issued Jul. 23, 1991; British patent applications GB 1,279,145, published Jun. 28, 1972 and GB 1,444,334, published Jul. 28, 1976; and PCT Application WO 91/07943, Chauduri, published Jun. 13, 1991; all such U.S. Patents herein by reference.

Since shaving, particularly daily shaving, can irritate the skin around the neck and face manufacturers of the shaving compositions often add ingredients to minimize skin irritation, and impart good skin feel both during and after shaving. These ingredients include humectants, emollients, and moisturizers. Such ingredients include aloe, menthol, lanolin, yucca, silicones, and other ingredients known for use in cosmetic compositons. Additional ingredients may be added to impart therapeutic benefits to the skin. These ingredients include antiseptics for treating razor cuts and nicks.

It is known in the art that silicone oils form a protective coating on the skin by filling the crevices and follicular openings of the skin. This protective coating reduces water loss through the stratum corneum and avoids tightening of the skin. Silicones are also thought to fill the cracks and crevices in the skin, resulting in skin smoother to the touch. Therefore, shaving compositions containing silicones not only reduce razor friction, but benefit the skin as well. Silicone oils, however, are typically difficult to incorporate into typical shaving compositions due their relative hydrophobicity. Therefore, in order to incorporate silicones into a typical aqueous-based shaving compositions, they must be modified to increase their hydrophilicity.

The preferable form silicones take when incorporated in shaving compositions are actually silicone polymers having acyloxyalkyl groups attached to the silicone backbone. These silicone copolymers, or polyorganosiloxanes, are hydrophilic non-ionic surfactants which can be easily incorporated into aqueous-based shaving composition. Silicone copolymer nonionic surfactants are disclosed in the art. Dow Corning's publication, *A Unique Marketing Proposition*, copyrighted 1987, discloses using Dow Corning 193 Dimethicone Copolyol (a dimethicone copolyol) in shaving creams. U.S. Pat. No. 5,034,220, Helioff et al. discloses using non-volatile polyethersiloxane copolymers, in shaving compositions for lubricating and protecting the skin during shaving. PCT Application WO 91/07943 discloses using polysiloxane polyether copolymers, i.e. dimethicone copolyols, in a shaving gel to improve the clarity and brightness of the gel.

The above mentioned art discloses adding a second non-ionic surfactant to shaving gels containing the silicone copolymer surfactant. The secondary non-ionic surfactant stabilizes the gel and improves the foam consistency of the lather created when the gel is rubbed onto the face. Furthermore, these secondary non-ionic emulsifiers act as wetting agents, thereby promoting good rinsing of the shaving lather from the razor and the skin. Typical secondary non-ionic surfactants include Oleth-10, Oleth-20, Ceteth-10, Ceteth-20; see PCT Application WO 91/07943.

SUMMARY OF THE INVENTION

The present invention is a post-foaming shaving gel composition comprising soap, a volatile liquid post-foaming agent, a silicone copolymer surfactant, and water, wherein the improvement is the removal of essentially all of the secondary non-ionic surfactant. Despite lacking a secondary non-ionic surfactant, these gel compositions have surprisingly good gel and foam stability. Furthermore, the shave gels of the present invention cause less skin irritation, and provide excellent skin conditioning benefits. These shaving gel compositions may additionally comprise known cosmetic ingredients including, but not limited to, gellants, humectants, emollients, colorings, and fragrances to improve the overall acceptability of the composition.

All the components disclosed herein are, unless specified otherwise, expressed as percent by total weight of the composition.

DETAILED DESCRIPTION OF THE INVENTION

The shaving gel compositions of the present invention comprises ingredients commonly known in the art. The following is a detailed description the components comprising the present invention.

Soaps

Soaps are a necessary component in forming the gel structure of the present invention. Furthermore, since these soaps are wetting agents, they provide excellent shaving conditions. The soaps used in the present invention are water soluble salts of higher fatty acids formed by combining fatty acids and base materials.

Fatty acids are used at levels from about 5% to about 35%, preferably 5% to about 20%, and most preferably from about 8% to about 16%. The fatty acids used herein are selected from the group consisting of $C_{10}$–$C_{24}$ fatty acids. Examples of these fatty acids include stearic, palmitic, myristic oleic, coconut oil, soya oil fatty acids, and mixtures thereof. Preferred are stearic, myristic, and palmitic acids. Most preferred are the stearic and palmitic acids. The level of base material used is from about 2% to about 18%, preferably from about 2% to about 10%, and most preferably from about 4% to about 8%, wherein the ration of the fatty acids to base material is about 4:1, preferably about 3:1 and most preferably about 2:1. The base materials are selected from the group consisting of mono-, di- and triethanolamine, iso-propanolamine, potassium hydroxide, sodium hydroxide, and mixtures thereof. Preferred are mono-, di-, and triethanolamine, most preferred is triethanolamine.

Therefore, the resulting soaps most preferred in this invention are palmitate soaps, stearate soaps, and combinations of palmitate and stearate soaps made by the reaction of triethanolamine with the respective fatty acid. The combination of soaps is from 1:5 to 5:1, preferably from 1:3 to 3:1, and most preferably from 3:1 palmitate to stearate.

All the above mentioned soaps may be prepared by any of the means known in the art.

Silicone Copolymer Surfactant

The silicone copolymer surfactants of the present invention are used at levels from about 0.2% to about 6%, preferably from about 0.5% to about 4%, and most preferably from about about 1% to about 3%. Said silicone copolymer surfactants correspond to the formula

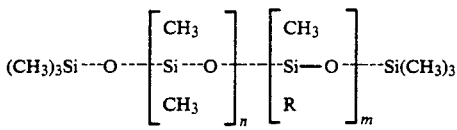

wherein R is $(CH_2)_3$—O—$(C_2H_4O)_x$—$(C_3H_6O)_y$—H ad the value of x is from 0 to about 50, preferably 8 to about 12, and most preferably about 10; the value of y is from 0 to about 50, preferably from 0 to about 2, and most preferably 0; the value of n is from about I to about 500, preferably from about 20 to about 90, and most preferably about 40; the value of m is from about 1 to about 10, preferably from about 2 to about 8, and most preferably about 5; a HLB value of from about 8 to about 20, preferably from about 10 to about 15, most preferably about 12.5; and a molecular weight from about 2,000 to about 50,000, preferably from about 3,000 to about 10,000, and most preferably about 3,100. Such silicone materials are disclosed in PCT Application WO 9107943, and are available as Dow Corning 193 Surfactant, from Dow Corning Corporation, Midland Mich.; and G.E. Silicone 218-1132, available from the General Electric Co., Silicone Products Division Waterford, New york.

Volatile Liquid Post-Foaming Agent

Volatile liquid post-foaming agents in the present invention transforms the gel into a foam by rapidly volitalizing upon rubbing the gel on the skin. The level of the liquid volatile post-foaming agents in the present invention is from about 1% to about 5%, preferably from about 2% to about 4%, and most preferably from about 2% to about 3%.

Liquid volatile foam-forming agents are known in the art and are disclosed in British Patent Application 1,279,145 published Jun. 28, 1972. Such agents are liquids or liquifiable saturated aliphatic hydrocarbons having from about 4 to 6 carbon atoms, such as n-pentane, isopentane, n-butane, isobutane, n-propane, isopropane, and mixtures thereof. In the present invention, isopentane and isobutane are preferred. Most preferred is a mixture of about 85% isopentane and about 15% isobutane. These volatile liquids may be supplemented with other volatile liquids or compressed non-liquified gases, commonly referred to as propellents, in order to assist in expulsion of the gel from the can. Such propellents are disclosed in British Patent Application 1,444,334 published Mar. 26, 1976.

Water

Water is typically used to form shaving gel compositions. There are no special requirements for the water used, except it must adequately solubilize the soap contained in the gel composition.

The level of water depends on what will produce an acceptable gel at typical temperatures the gel is used at, and the other ingredients that go into the formula. In this invention, water is added in a sufficient amount to Q.S. the formulation to 100%. Typically, the level of water is from about 60% to about 75% of the gel composition.

Optional Components

The shaving gel of the present invention may contain various components making the composition more acceptable to the consumer. Many of the components known in the art may be used in conjunction with the present invention.

a. Gellants

Gellants may be included in the shaving gel formulation of the present invention. These gellants, particularly those derived from cellulosic materials, improve the consistency of the gel and its thermal stability, and provides increased lubricity to the foam.

Gellants, and their levels, are selected by their ability to adjust the viscosity of the composition. Viscosity is adjusted up or down in order to provide the gel with body, but not so much as to make it difficult to spread over the face. The viscosity also is critical for keeping the post-forming agent into the gel.

The gel composition of the present invention have viscosities between about 15,000 cps and about 60,000 cps, preferably from about 20,000 cps to about 40,000 cps. Said viscosity is measured with a cone and plate viscometer such as a Wells Brookfield Viscometer, which is run at 1 RPM with a $S_2$ spindle.

To achieve the above viscosities, gellants are used in the present invention in amounts up to about 2%, but preferably, no greater than 1%. These gellants are selected from the group consisting of alkyl glycols, polyacrylic acids, alkyl modified cellulose polymers, guar gums, xantham gums, and mixtures thereof. Preferred gellants in the present invention are alkyl modified cellulose polymers, specifically those selected from the group consisting of methylcellulose, ethylcellulose, hydroxybutyl methylcellulose, hydroxy ethylcellylose, hydroxy propylcellulose, hydroxypropyl methylcellulose cellulose, and mixtures thereof. Most preferred in the present invention are hydroxy ethylcellulose, hydroxy propylcellulose, hydroxypropyl methylcellulose, and mixtures thereof. Such gellants are available from Dow Chemical USA.

In addition to these cellulosic materials other traditional gellants preferred for use herein include the alkyl glycols, specifically polyethylene glycol.

b. Emollients

Emollients used in the present invention provide a source of lipids to replace those lost during shaving. They also may be used to soften whiskers to make them easier to cut, and scavenge for irritating basic materials in the gel matrix.

Emollients may be used in the present at levels from about 1% to about 5%, preferably from about 2% to about 4%, most preferably at about 2.75%. The emollients selected are those generally known in the art and can be found in a number of cosmetic formularies such as Harry's Cosmeticology, Edited by Wilkinson and Moore, 7th Ed. 1982. The emollients useful in the present invention include glycol esters. The glycol esters are selected from the group consisting of propylene glycol monoisostearate, propylene glycol dipelargonate, propylene glycol oleate, propylene glycol myristate, and mixtures thereof. Most preferred is propylene glycol monoisostearate.

c. Humectants

Humectants may be included in the gel formulation of the present invention. Humectants serve to bind water thus reducing the tendency of the gel's foam to dry out and collapse. Humectants may be used at levels from about 2% to about 12%, preferably from about 5% to about 7%, most preferably at 6%. Humectants useful in the present invention are those generally known in the art and can be found in a number of cosmetic formularies such as Harry's Cosmeticology, Edited by Wilkinson and Moore, 7th Ed. 1982. The humectants useful in the present invention include polyhydric alcohols selected from the group consisting of ethylene glycol, propylene glycol, butylene glycol, glycerin, and sorbitol. Most preferred in the present invention are sorbitol and propylene glycol.

d. Colorants

Colorants may be added to compositions of the present invention. The colorants should be used in very low levels to avoid staining the skin or towels. In the present invention, dyes are used at levels from about 0.1% to about 0.4% of a 0.5% solution of dye, preferably about 0.2%. Dyes or colorants include any of those approved for use such as D&C or FD&C dyes; for example FD&C Blue #1.

e. Fragrance

Fragrances may be added to the gel composition of the present invention. The level of fragrance used is dictated by the aesthetic affect sought by the formulator. In the present invention, the level of fragrance may be as high as about 1%, preferably no more than 0.5%. These fragrances or perfumes should be compatible with water-soluble soaps.

f. Miscellaneous Ingredients

The shaving gel of the present invention is not limited to the ingredients above. Other ingredients can be added as deemed appropriate by the formulator. Such ingredients include preservatives, cooling agents corrosion inhibitors, bacteriostats, pilmotor agents, and other ingredients found in shaving compositions known in the art.

EXAMPLES

| Shaving gel compositions: Component | Weight Example | | | |
|---|---|---|---|---|
|  | #1 | #2 | #3 | #4 |
| Triethanolamine | 6.00 | 6.00 | 7.00 | 5.40 |
| Palmitic Acid | 0.00 | 13.00 | 7.00 | 7.20 |
| Stearic Acid | 13.00 | 0.00 | 7.00 | 2.40 |
| Silicone Copolymer Surfactant* | 1.00 | 2.00 | 1.00 | 2.00 |
| Propylene Glycol Monoisostearate | 2.50 | 2.75 | 1.80 | 2.75 |
| Polyethylene Glycol 600,000** | 0.25 | 0.40 | 0.20 | 0.25 |
| Sorbitol (70%) | 8.00 | 6.00 | 2.00 | 4.00 |
| Propylene Glycol | 2.00 | 2.00 | 8.00 | 2.00 |
| Hydroxypropylcellulose*** | 0.05 | 0.10 | 0.08 | 0.075 |
| Color Solution (FD & C Blue #1 @ .5%) | 0.20 | 0.20 | 0.20 | 0.20 |
| Fragrance | 0.35 | 0.35 | 0.35 | 0.35 |
| Isopentane | 2.34 | 1.53 | 2.55 | 1.87 |
| Isobutane | 0.41 | 0.27 | 0.45 | 0.33 |
| Water Q.S. to 100% | | | | |

*GE Silicone 218-1132, available from the General Electric Co. Silicone Products Division; and Dow 193 available from the Dow Corning Company
**Polyoy WSR-N-205, available from Amerchol Corp.
***Klucel-HF, available from the Aqualon Company The compositions above are made according to the following method:

Add approximately 70% water and the polyethylene glycol to a jacketed vessel. Heat the mixture to about 70° C., and add the silicone copolymer surfactant, palmitic acid, stearic acid, sorbitol, propylene glycol, and propylene glycol monoisostearate, stirring the mixture until it is smooth. Add in separate steps with stirring, hydroxypropylcellulose and triethanolamine. After the mixture is uniform, cool the mixture to about 45° C. Add the fragrance and cool the mixture to about 3° C. Add isopentane and isobutane, and Q.S. the mixture to 100% with water.

We claim:

1. A post-foaming shaving gel composition comprising:
   (a) from about 5% to about 35% of a $C_{10}$–$C_{24}$ fatty acid;
   (b) from about 2% to about 18% of a base material selected from the group consisting of mono-, di- and tirethanoamine, iso-propanolamine, potassium hydroxide, sodium hydroxide, and mixtures thereof;
   (c) from about 2% to about 6% of a silicone copolymer surfactant;
   (d) from about 1% to about 5% of a volatile liquid post foaming agent selected to transform the gel into a foam upon rubbing the gel on the skin; and
   (e) water;

wherein the composition is essentially free of a secondary nonionic surfactant, and the ratio of fatty acid to base material is about 4:1, and the silicon copolymer surfactant is a polysiloxane polyether copolymer corresponding to the formula

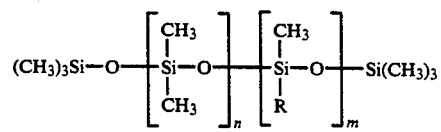

wherein R is $(CH_2)_3$—O—$(C_2H_4O)_x$—$(C_3H_6O)_y$—H and the value of x is from 0 to about 50, the value of y is from 0 to about 50, the value of n is from about 1 to about 500, the value of m is from about 1 to about 10, the HLB value is from about 8 to about 20, and the molecular weight is from about 2,000 to about 50,000.

2. A post-foaming shaving gel composition according to claim 1, wherein the base is selected from the group consisting of mono-, di-, triethanolamine, and mixtures thereof.

3. A post-foaming shaving gel composition according to claim 2 wherein the base is triethanolamine.

4. A post-foaming shaving gel composition according to claim 1, wherein the fatty acid is selected from the group consisting of palmatic acid, stearic acid, myristic acid, oleic acid, coconut oil fatty acid, soya oil fatty acid, and mixture thereof.

5. A post-foaming shaving gel composition according to claim 4 wherein the fatty acids are selected from the group consisting of palmatic acid, stearic acid, myristic acid, and mixtures thereof.

6. A post-foaming shaving gel composition according to claim 1 wherein the volatile liquid post-foaming agent is selected from the group consisting of n-pentane, isopentane, n-butane, isobutane, n-propane, isopropane, and mixtures thereof.

7. A post-foaming shaving gel composition according to claim 6 wherein the volatile liquid post-foaming agent is a mixture of about 85% isopentane to about 15% isobutane.

8. A post-foaming shaving gel composition according to claim 1 comprising:
   (a) from about 5% to about 20% of the $C_{10}-C_{24}$ fatty acid;
   (b) from about 2% to about 10% of the base material;
   (c) from about 0.5% to about 4% of the silicone copolymer surfactant;
   (d) from about 2% to about 4% of the volatile liquid post-foaming agent; and
   (e) water;
wherein the composition is essentially free of a secondary nonionic surfactant, and the ratio of fatty acid to base material is about 3:1, and the silicone copolymer surfactant is a polysiloxane polyether copolymer corresponding to the formula

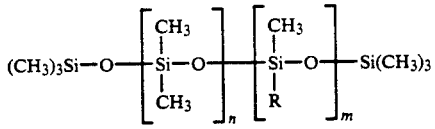

wherein R is $(CH_2)_3-O-(C_2H_4O)_x-(C_3H_6O)_y-H$ and the value of x is from 8 to about 12, the value of y is from 0 to about 2, the value of n is from about 20 to about 90, the value of m is from about 2 to about 8, the HLB value is from about 10 to about 15, and the molecular weight is from about 3,000 to about 10,000.

9. A post-foaming shaving gel composition according to claim 8 wherein the fatty acids are selected from the group consisting of palmatic acid, stearic acid, myristic acid, and mixtures thereof.

10. A post-foaming shaving gel composition according to claim 9 wherein the base is triethanolamine.

11. A post-foaming shaving gel composition according to claim 10 wherein the volatile liquid post-foaming agent is a mixture of about 85% isopentane to about 15% isobutane.

12. A post-foaming shaving gel composition according to claim 8 additionally comprising gellants, emollients, and humectants.

13. A post-foaming shaving gel composition according to claim 12 wherein the gellants are at a level from 0% to about 2%.

14. A post-foaming shaving gel composition according to claim 13 wherein the gellants are selected from the group consisting of methylcellulose, ethylcellulose, hydroxybutyl methylcellulose, hydroxy ethylcellylose, hydroxy propylcellulose, hydroxypropyl methylcellulose cellulose, and mixtures thereof.

15. A post-foaming shaving gel composition according to claim 12 wherein the emollients are at a level from about 1% to about 5%.

16. A post-foaming shaving gel composition according to claim 15 wherein the emollients are glycol esters selected from the group consisting of propylene glycol monoisostearate, propylene glycol dipelargonate, propylene glycol oleate, propylene glycol myristate, and mixtures thereof.

17. A post-foaming shaving gel composition according to claim 12 wherein the humectants are at a level from 2% to about 12%.

18. A post-forming shaving gel composition according to claim 17 wherein the humectants are polyhydric alcohols selected from the group consisting of ethylene glycol, propylene glycol, butylene glycol, glycerin, and sorbitol.

19. A post-foaming shaving gel composition comprising:
   (a) from about 8% to about 16% of a $C_{10}-C_{24}$ fatty acid;
   (b) from about 4% to about 8% of a base material selected from the group consisting of mono-, di- and triethanolamine, iso-propanolamine, potassium hydroxide, sodium hydroxide, and mixtures thereof;
   (c) from about 1% to about 3% of a silicone copolymer surfactant;
   (d) from about 2% to about 3% of a volatile liquid post-foaming agent selected to transform the gel into a foam upon rubbing the gel on the skin;
   (e) from 0% to about 1% gellant;
   (f) from about 2% to about 4% emollient;
   (g) from about 5% to about 7% humectant;
   (h) from about 0.1% to about 0.4% colorant;
   (i) from 0% to abut 1% fragrance; and
   (j) water,
wherein the composition is essentially free of a secondary nonionic surfactant, and the ratio of fatty acid to base material is about 2:1 and the silicone copolymer surfactant is a polysiloxane polyether copolymer corresponding to the formula

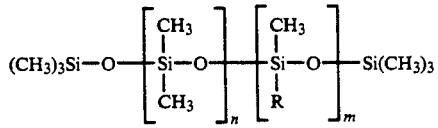

wherein R is $(CH_2)_3-O-(C_2H_4O)_x-(C_3H_6O)_y-H$ and the value of x is about 10, the value of y is 0, the value of n is about 40, the value of m is about 5, the HLB value is about 12.5, and the molecular weight is about 3,100.

* * * * *